US007311935B2

(12) United States Patent
Laloi et al.

(10) Patent No.: US 7,311,935 B2
(45) Date of Patent: Dec. 25, 2007

(54) CARBOXYPEPTIDASE OF COCOA

(75) Inventors: Maryse Laloi, Lausanne (CH); James McCarthy, Noizay (FR); Peter Bucheli, Shanghai (CN)

(73) Assignee: Nestec S.A., Vevey (CH)

( * ) Notice: Subject to any disclaimer, the term of this patent is extended or adjusted under 35 U.S.C. 154(b) by 0 days.

(21) Appl. No.: 11/268,342

(22) Filed: Nov. 7, 2005

(65) Prior Publication Data

US 2006/0068060 A1 Mar. 30, 2006

Related U.S. Application Data

(60) Division of application No. 10/382,239, filed on Mar. 5, 2003, which is a continuation-in-part of application No. PCT/EP02/07162, filed on Jun. 28, 2002.

(30) Foreign Application Priority Data

Jul. 6, 2001 (EP) ............... 01116407

(51) Int. Cl.
  *A23G 1/00* (2006.01)
  *C12N 9/00* (2006.01)
  *C12N 9/48* (2006.01)
  *C12N 1/20* (2006.01)
  *C07H 21/04* (2006.01)

(52) U.S. Cl. ............. 426/584; 426/593; 426/631; 435/183; 435/212; 435/252.3; 435/320.1; 536/23.2

(58) Field of Classification Search ......... 435/183, 435/212, 252.3, 320.1; 536/23.2; 426/584, 426/593, 631
See application file for complete search history.

(56) References Cited

U.S. PATENT DOCUMENTS 5,888,562 A 3/1999 Hansen et al.
2003/0219511 A1 11/2003 Laloi et al.

2006/0068060 A1 3/2006 Laloi et al.

FOREIGN PATENT DOCUMENTS

EP 0749694 12/2006

OTHER PUBLICATIONS

Li et al. Accession AY072822. Dec. 4, 2002.*
Bytof, G. et al., "Specificity and Stability of the Carboxypeptidase activity in Ripe Ungerminated Seeds of Theobroma Cacao L," Food Chemisty, vol. 54, No. 1, pp. 15-21, (1995).
Blinkovsky, Alexander M. et al., "Purification, Characterization, and Heterologous Expression in Fusarium Venenatum of a Novel Serine Carboxypeptidase From *Aspergillus oryzae*," Applied and Environmental Microbiology, vol. 65, No. 8, pp. 3298-3303, (1999).
Voigt et al., "In-Vitro Formation of Cocoa-Specific Aroma Precursors: Aroma-Related Peptides Generated From Cocoa-Seed Protein by Cooperation of an Aspartic Endoprotease and a Carboxypeptidase," Food Chemistry, vol. 49, No. 2, pp. 173-180, (1994).
Amin, I. et al., "Proteolytic Activity (Aspartic Endoproteinase and Carboxypeptidase) of Cocoa Bean During Fermentation," Journal of the Science of Food and Agriculture, vol. 76, No. 1, pp. 123-128, (1998).
Li et al. AY072822 (2002).
Quensel, V.C. et al., "Agents Inducing the Death of Cacao Seeds During Fermentation," J. Sci. Fd Agric., vol. 16, pp. 441-447, (1965).
Ostovar, K. and Keeney, P.G., "Isolation and Characterization of Microorganisms Involved in the Fermentation of Trinidad's Cacao Beans," Journal of Food Science, vol. 38, pp. 611-617 (1973).
Kirchhoff, P.M. et al., "Peculiarity of the Accumulation of Free Amino Acides During Cocoa Fermentation," Food Chemistry, vol. 31, pp. 295-311, (1989).

* cited by examiner

*Primary Examiner*—Tekchand Saidha
*Assistant Examiner*—Christian L. Fronda
(74) *Attorney, Agent, or Firm*—Bell, Boyd & Lloyd LLP (57) ABSTRACT

The present invention relates to a novel carboxypeptidase gene and the polypeptide encoded thereby. In particular, the present invention relates to the use of the present carboxypeptidase and polypeptide in the manufacture of cocoa flavor and/or chocolate.

4 Claims, 4 Drawing Sheets

FIG. 3A — Cacao — Barley CP-MI  
Residues position

FIG. 3B — Cacao — Barley CP-MII  
Residues position

FIG. 3C — Cacao — Barley CP-MIII  
Residues position

CARBOXYPEPTIDASE OF COCOA

PRIORITY CLAIM

This application is a divisional of and claims the benefit of U.S. patent application Ser. No. 10/382,239 filed Mar. 5, 2003, which is a continuation-in-part of the US national phase designation of International application PCT/EP02/07162 filed Jun. 28, 2002, the contents of which are expressly incorporated herein by reference thereto.

BACKGROUND

The present invention relates to a novel carboxypeptidase gene and the polypeptide encoded thereby. In particular, the present invention relates to the use of the present carboxypeptidase in the manufacture of cocoa flavor and/or chocolate.

It is known that in processing *cacao* beans the generation of the typical cocoa flavor requires two steps: a fermentation step, which includes air-drying of the fermented material, and a roasting step.

During fermentation, two major activities may be observed. First, the pulp surrounding the beans is degraded by micro-organisms with the sugars contained in the pulp being largely transformed to acids, especially acetic acid (Quesnel et al., J. Sci. Food. Agric. 16 (1965), 441-447; Ostovar and Keeney, J. Food. Sci. 39 (1973), 611-617). The acids then slowly diffuse into the beans and eventually cause an acidification of the cellular material. Second, fermentation also results in a release of peptides exhibiting differing sizes and a generation of a high level of hydrophobic free amino acids. This latter finding led to the hypothesis that proteolysis occurring during the fermentation step is not due to a random protein hydrolysis, but seems to be rather based on the activity of specific endoproteinases (Kirchhoff et al., Food Chem 31 (1989), 295-311). This specific mixture of peptides and hydrophobic amino acids is deemed to represent cocoa-specific flavor precursors.

Until now several proteolytic enzyme activities have been investigated in *cacao* beans and studied for their putative role in the generation of cocoa flavor precursors during fermentation.

An aspartic endoproteinase activity, which is optimal at a very low pH (pH 3.5) and inhibited by pepstatin A, has been identified. A polypeptide described to have this activity has been isolated and is described to consist of two peptides (29 and 13 kDa) which are deemed to be derived by self-digestion from a 42 kDa pro-peptide (Voigt et al., J. Plant Physiol. 145 (1995), 299-307). The enzyme cleaves protein substrates between hydrophobic amino acid residues to produce oligopeptides with hydrophobic amino acid residues at the ends (Voigt et al., Food Chem. 49 (1994), 173-180). The enzyme accumulates with the vicilin-class (7S) globulin during bean ripening. Its activity remains constant during the first days of germination and does not decrease before the onset of globulin degradation (Voigt et al., J. Plant Physiol. 145 (1995), 299-307).

Also, a cysteine endoproteinase activity had been isolated which is optimal at a pH of about 5. This enzymatic activity is believed not to split native storage proteins in ungerminated seeds. Cysteine endoproteinase activity increases during the germination process when degradation of globular storage protein occurs. To date, no significant role for this enzyme in the generation of cocoa flavor has been reported (Biehl et al., Cocoa Research Conference, Salvador, Bahia, Brasil, 17-23 Nov. 1996).

Moreover, a carboxypeptidase activity has been identified which is inhibited by PMSF, and thus belongs to the class of serine proteases. It is stable over a broad pH range with a maximum activity at pH 5.8. This enzyme does not degrade native proteins, but preferentially splits hydrophobic amino acids from the carboxy-terminus of peptides (Bytofet at., Food Chem. 54 (1995), 15-21).

During the second step of cocoa flavor production, the roasting step, the oligopeptides and amino acids generated at the stage of fermentation are obviously subjected to a Maillard reaction with reducing sugars present in fermented beans, eventually yielding substances responsible for the cocoa flavor as such.

In the art, there have been many attempts to artificially produce cocoa flavor.

Cocoa-specific aroma has been obtained in experiments wherein acetone dry powder (AcDP) prepared from unfermented ripe *cacao* beans was subjected to autolysis at a pH of 5.2 followed by roasting in the presence of reducing sugars. It was conceived that under these conditions preferentially free hydrophobic amino acids and hydrophilic peptides should be generated and the peptide pattern thus obtained was found to be similar to that of extracts from fermented *cacao* beans. An analysis of free amino acids revealed that Leu, Ala, Phe and Val were the predominant amino acids liberated in fermented beans or autolysis (Voigt et al., Food Chem. 49 (1994), 173-180). In contrast to these findings, no cocoa-specific aroma could) be detected when AcDP was subjected to autolysis at a pH of as low as 3.5 (optimum pH for the aspartic endoproteinase). Only few free amino acids were found to be released, but a large number of hydrophobic peptides were formed. When peptides obtained after the autolysis of AcDP at a pH of 3.5 were treated with carboxypeptidase A from porcine pancreas at pH 7.5, hydrophobic amino acids were preferentially released. The pattern of free amino acids and peptides was similar to that found in fermented *cacao* beans and to the proteolysis products obtained by autolysis of AcDP at pH 5.2. After roasting of the amino acids and peptides mixture as above, a cocoa aroma could be generated.

It has also been shown that a synthetic mixture of free amino acids alone, with a similar composition to that of the spectrum found in fermented beans, was incapable of generating cocoa aroma after roasting, indicating that both the peptides and the amino acids are important for this purpose (Voigt et al., Food Chem. 49 (1994), 173-180.

In view of the above data, a hypothetical model for the generation, during fermentation, of the said mixture of peptides and amino acids, i.e. the *cocoa* flavor precursors, had been devised (FIG. 1), where in a first step peptides having a hydrophobic amino acid at their end, are formed from storage proteins, which peptides are then further degraded to smaller peptides and free amino acids. To produce the said peptides having C-terminal hydrophobic amino acids, an aspartic endoproteinase activity related to that mentioned above seems to be involved. Yet, for splitting off hydrophobic amino acids from peptides formed in the preceding step the only known enzymatic activity, which might be considered in this respect, is that of a carboxypeptidase. However, such enzyme has not been isolated and studied in detail in *cacao,* and it is therefore still questionable which *cacao* enzyme might be responsible for the generation of hydrophobic amino acids required for cocoa flavor.

Though some aspects of cocoa flavor production have been elucidated, so far there is still a need in the art to fully understand the processes involved, so that the manufacture of cocoa flavor may eventually be optimized.

SUMMARY

The present invention provides means for further elucidating the processes involved in the formation of cocoa-specific aroma precursors during the fermentation of *cacao* seeds, to improve the formation of cocoa flavor during processing and manufacturing and eventually providing means assisting in the artificial production of cocoa flavor.

This problem has been solved by providing a nucleotide sequence encoding a novel carboxypeptidase from *cacao* beans (termed *cacao* CP-III), which is identified by SEQ. ID. No. 1, or functional derivatives thereof having a degree of homology that is greater than 80%, preferably greater than 90% and more preferably greater than 95%.

It will be appreciated by the skilled person that a gene encoding a specific polypeptide may differ from a given sequence according to the Wobble hypothesis, in that nucleotides are exchanged that do not lead to an alteration in the amino acid sequence. Yet, according to the present invention, also nucleotide sequences shall be embraced which exhibit a nucleotide exchange leading to an alteration of the amino acid sequence such that the functionality of the resulting polypeptide is not essentially disturbed.

This nucleotide sequence may be used to synthesize a corresponding polypeptide by means of recombinant gene technology, in particular, a polypeptide as identified by SEQ. ID. No. 2.

As has been shown in a comparison with other carboxypeptidases from other plants, the present enzyme does not show a substantial homology to any of the carboxypeptidases known so far. Since it is assumed, that cocoa may furthermore contain additional carboxypeptidases that might exhibit a higher homology to the carboxypeptidases known so far, it must be considered as a surprising fact that this very enzyme has been detected.

For producing the polypeptide by recombinant means, the nucleotide of the present invention is included in an expression vector downstream of a suitable promoter and is subsequently incorporated into a suitable cell which may be cultured to yield the polypeptide of interest. Suitable cells for expressing the present polypeptide include bacterial cells, such as e.g. *E. coli*, or yeast, insect, mammalian or plant cells.

The present DNA sequence may also be incorporated directly into the genome of the corresponding cell by techniques well known in the art, such as e.g. homologous recombination. Proceeding accordingly will provide a higher stability of the system and may include integration of a number of said DNA-sequences into a cell's genome.

The cells thus obtained may in consequence be utilized to produce the polypeptide in batch culture or using continuous procedures, with the resulting polypeptide being isolated according to conventional methods.

The recombinant carboxypeptidase obtained may be used for the manufacture of cocoa flavor. To this end, the enzyme described herein may be utilized in an artificial trial run wherein a mixture of different proteins, such as *cacao* storage proteins, or protein hydrolysates of other resources, are subjected to enzymatic degradation by means of enzymes known to be involved in proteolytic degradation to eventually assist in the production of flavor precursors. The enzyme may likewise also be utilized in the production of cocoa liquor and in the manufacture of chocolate.

Yet, the present invention also provides plants, in particular *cacao* plants, comprising a recombinant cell containing one or more additional copies of the carboxypeptidase of the present invention. Such a *cacao* plant will produce beans, which will exhibit a modified degradation of storage proteins when subjected to the fermentation process, allowing a more rapid degradation or a pattern of hydrolysis that yields a higher level of cocoa flavor precursor since a higher amount of carboxypeptidase will be present.

The carboxypeptidase of the present invention may also be used to produce other transgenic plants, such as soybean and rice, producing seeds with this new protein modifying enzyme.

Additional features and advantages are described herein, and will be apparent from, the following Detailed Description and the figures.

DETAILED DESCRIPTION

As described above, it was suggested that a carboxypeptidase could be involved in the production of cocoa flavor precursors during *cacao* fermentation. However, it was not known in the art which cacao carboxypeptidase carried out this function considering that five classes of carboxypeptidases (Type I-V) have been identified in different plants by references to differences in substrate specificities, molecular weights and chromatographic profiles. Furthermore, 50 sequences having homologies with serine carboxypeptidases exist in the completed *Arabidopsis* genome.

Figure 1:
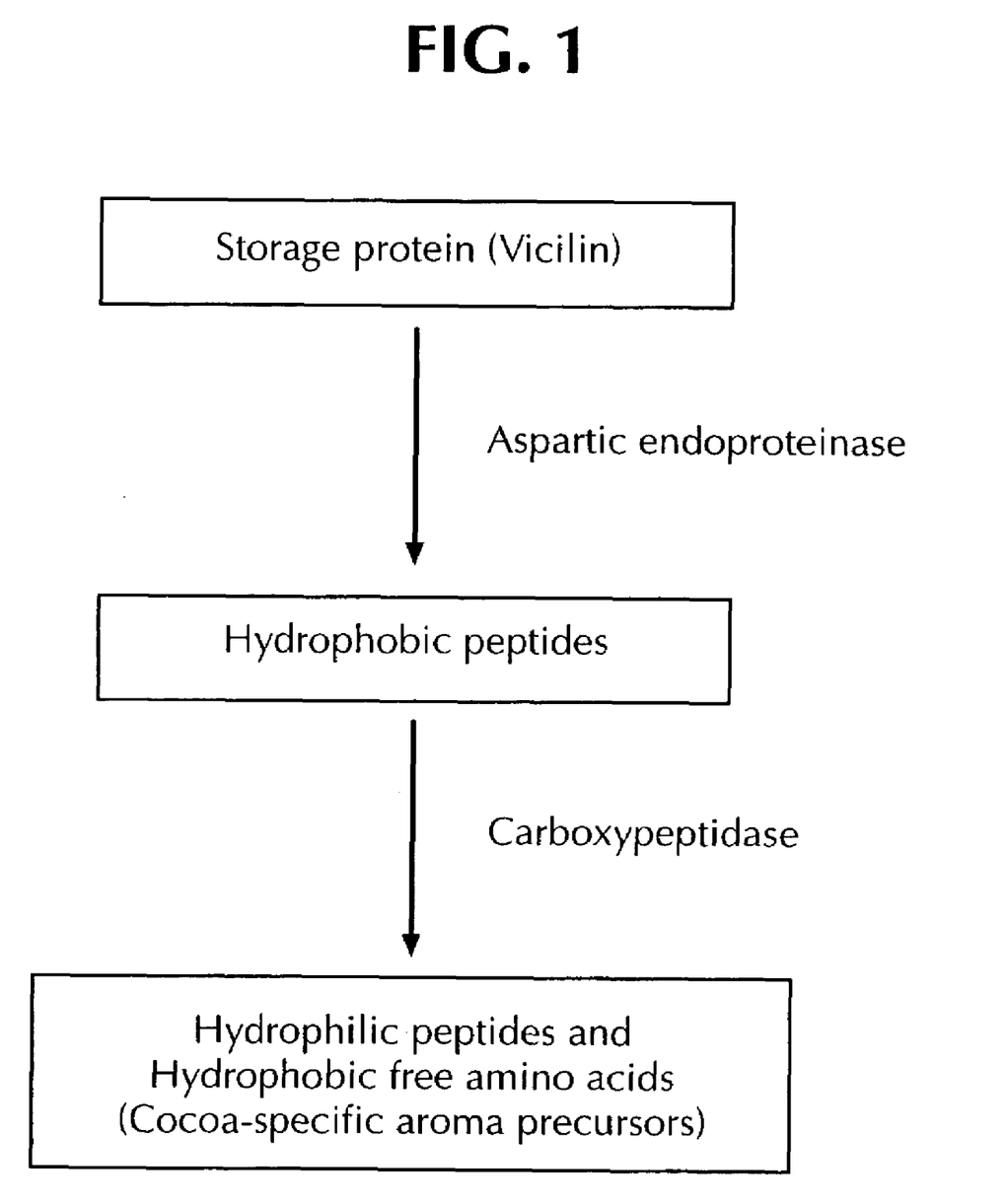
FIG. 1 shows a scheme illustrating a potential process for the proteolytic formation of cocoa-specific aroma.

The proteoleytic formation of cocoa-specific aroma according to the invention is illustrated in FIG. 1.

The following examples illustrate the invention further without limiting it thereto. In the examples, the following abbreviations have been used:

PCR: Polymerase Chain Reaction
RACE: Rapid Amplification cDNA Ends
cDNA: complementary deoxyribonucleic acid
mRNA: messenger ribonucleic acid
DEPC: Diethyl pyrocarbonate
3,4-DCI: 3,4-dichloroisocoumarin

EXAMPLES

Materials

Cacao (*Theobroma cacao* L.) seeds (male parent unknown) from ripe pods of clone ICS 95 were provided by Nestlé ex-R&D Center Quito (Ecuador). The seeds were taken from the pods immediately after arrival at Nestle Research Center Tours (4-5 days after harvesting). The pulp and the seed coat were eliminated, and the cotyledons were frozen in liquid nitrogen and stored at −80° C. until use.

Preparation of mRNA

Total RNA was prepared using the following method. Two seeds were ground in liquid nitrogen to a fine powder and extraction was directly performed with a lysis buffer containing 25 mM Tris HCl pH8, 25 mM EDTA, 75 mM NaCl, 1% SDS and 1M 3-mercaptoethanol. RNA was extracted with one volume of phenol/chloroform/isoamylalcohol (25/24/1) and centrifuged at 8000 rpm, 10 min at 4° C. The aqueous phase was extracted a second time with one volume of phenol/chloroform/isoamylalcohol (25/24/1). RNA was precipitated with 2M lithium chloride at 4° C. overnight. The RNA pellet obtained after centrifugation was resuspended in DEPC-treated water, and a second precipitation with 3M sodium acetate pH 5.2 was performed in presence of two volumes of ethanol. The RNA pellet was washed with 70% ethanol and resuspended in DEPC-treated water. Total RNA was further purified using the Rneasy Mini kit from Qiagen®.

Cloning of a Carboxypeptidase cDNA

Cloning Strategy

Figure 2:
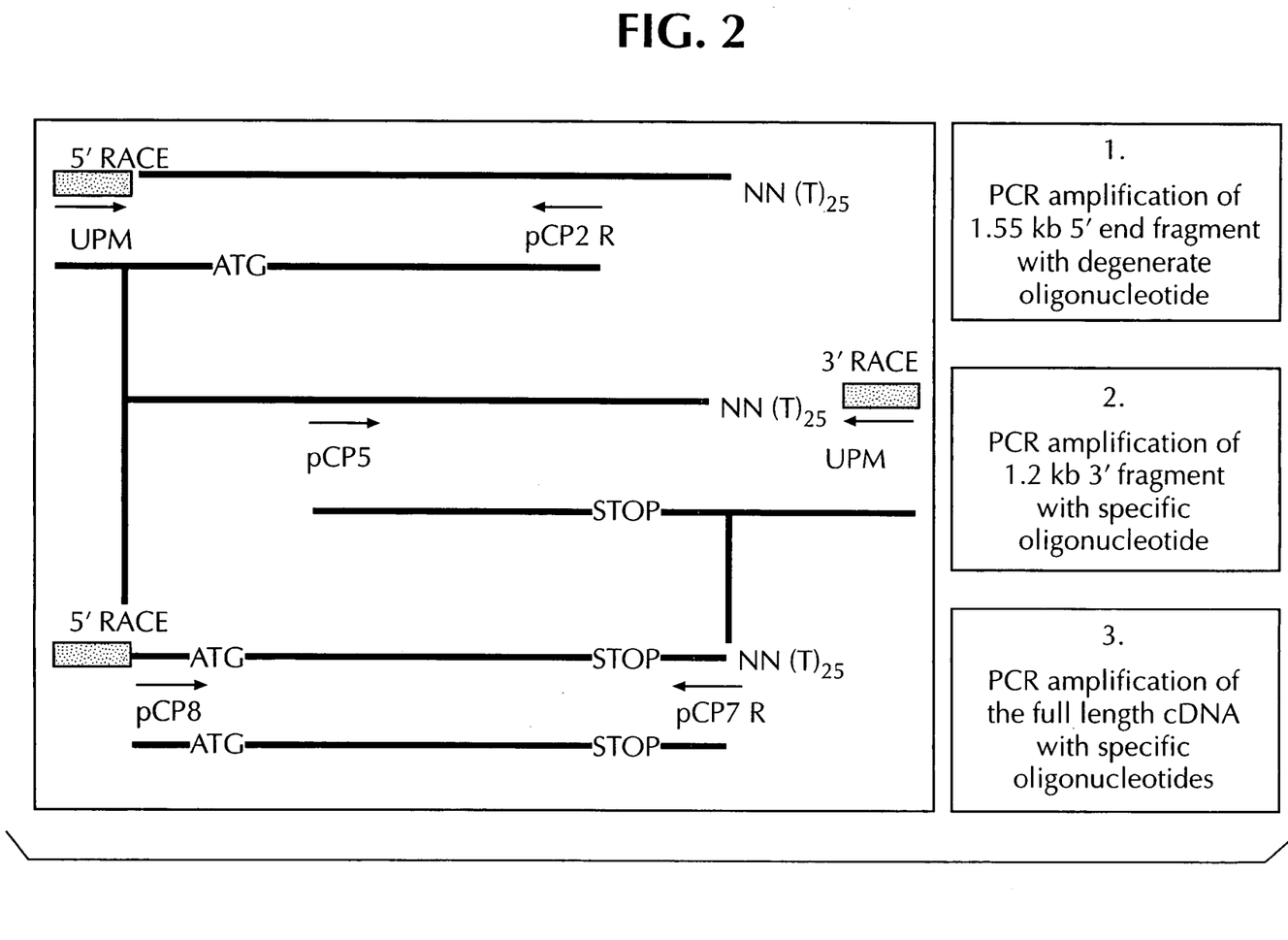
FIG. 2 shows the cloning strategy used for the isolation of a cDNA encoding a carboxypeptidase from *Theobroma cacao*.

A 1.5 kb 5'-end fragment of a carboxypeptidase from *cacao* seed was amplified by RT-PCR using a degenerate oligonucleotide. Based on the sequence of this fragment, a primer was designed to amplify a 3'-end fragment. Finally, a full-length cDNA (*cacao* CP-III) was amplified using primers specific to both extremities. The cloning strategy used for isolation of a cDNA encoding a carboxypeptidase from *Theobroma cacao*, clone ICS 95 is shown in FIG. 2.

Primer Design

A search for carboxypeptidase sequences in the GenBank database led to the identification of several plant sequences. A multiple alignment of these sequences revealed the presence of conserved regions. The conserved sequence MVP-MDQP located near the histidine catalytic site has been used to design a degenerate oligonucleotide in the antisense orientation: pCP2r (5'-GGYTGRTCCATNGGNACCAT) (SEQ ID No. 3).

Synthesis of cDNA

Total RNA (see above) was used to synthesize first strand 3' and 5' cDNAs with the SMART™ RACE cDNA Amplification Kit (Clontech, USA). Synthesis has been performed exactly as described in the kit instructions using 1 µg of total RNA and the Superscript™ II MMLV reverse transcriptase (Gibco BRL, USA). After synthesis, cDNAs were used directly for PCR or kept at −20° C.

5' RACE Amplification

Specific cDNA amplification was performed with 2.5 µl of the first strand 5' cDNA in 50 µl buffer containing: 40 mM Tricine-KOH, pH 8.7, 15 mM KOAc, 3.5 mM Mg(OAc)$_2$, 3.75 µg/ml BSA, 0.005% Tween-20, 0.005% Noninet-P40, 0.2 mM dNTP's, 14 pmoles of pCP2r primer, 5 µl of 10× Universal primer Mix (UPM) and 1 µl 50× Advantage 2 polymerase Mix (Clontech, USA). Amplification was performed in a Bio-med thermocycler 60 (B. Braun). A first denaturation step (94° C., 2 min) was followed by 35 cycles of denaturation (94° C., 1 min), primer annealing (55° C., 1.5 min) and extension (72° C., 2 min). The extension time was increased by 3 sec at each cycle. Amplification was ended by a final extension step (72° C., 10 min). The amplified fragment was cloned in pGEM®-T vector and sequenced.

3' RACE PCR

The sequence information obtained after the sequencing of the 5' end fragment was used to design a specific oligonucleotide pCP5 (5'-GCTTTTGCTGCCCGAGTC-CACC) (SEQ ID No. 4), which was used for 3'-RACE amplification. 3'-RACE PCR was performed with 2.5 µl of SMART single strand 3' cDNA in 50 µl buffer containing 40 mM Tricine-KOH pH 8.7, 15 mM KOAc, 3.5 mM Mg (OAc)$_2$, 3.75 µg/ml BSA, 0.005% Tween-20, 0.005% Noninet-P40, 0.2 mM dNTP's, 10 pmoles of pCP5 primer, 10 µl of 10× Universal primer Mix (UPM) and 1 µl 50× Advantage 2 polymerase Mix (Clontech, USA). Amplification was performed via touchdown PCR, in a Bio-med thermocycler 60 (B. Braun).

A first denaturation step (94° C., 1 min) was followed by:
  5 cycles including denaturation at 94° C. for 30 sec and annealing/extension at 72° C. for 3 min
  5 cycles including denaturation at 94° C. for 30 sec and annealing/extension at 70° C. for 30 sec and 72° C. for 3 min
  30 cycles including denaturation at 94° C. for 30 sec and annealing/extension at 68° C. for 30 sec and 72° C. for 3 min.

The amplified fragment was cloned in pGEM®-T vector and sequenced.

Full Length cDNA

The sequence information obtained after the sequencing of 5'-and 3'-RACE fragments was used to design two specific oligonucleotides.

pCP8:  A sense primer           (SEQ ID No. 5)
       (5'-CAAAGAGAAAAAGAAAAGATGGC)

pCP7r: A reverse primer         (SEQ ID No. 6)
       (5'-CCCCAGAGCTTTACGATACGG).

PCR reaction was performed with 2.5 µl first strand cDNA in 50 pl buffer containing: 40 mM Tricine-KOH pH 8.7, 15 mM KOAc, 3.5 mM Mg(OAc)$_2$, 3.75 µg/ml BSA, 0.005% Tween-20, 0.005% Noninet-P40, 0.2 mM dNTP's, 10 pmoles of pCP8 primer, 10 pmoles of pCP7r primer and 1 µl 50× Advantage 2 polymerase Mix (Clontech, USA). Amplification was performed in a Bio-med thermocycler 60 (B. Braun). A first denaturation step (94° C., 1 min) was followed by 35 cycles of denaturation (94° C., 30 sec), primer annealing (63° C., 1 min) and extension (72° C., 2 min). The extension time was increased by 3 sec at each cycle. Amplification was ended by a final extension step (72° C., 10 min). The amplified fragment was cloned in pGEM®-T Easy vector and sequenced.

Sequencing and Analysis of DNA Sequences cDNA sequencing has been performed by Eurogentech (Belgium) and ESGS (France). Sequence analysis and comparison were performed with Lion's software bioScout, Lasergene software (DNAStar) and Genedoc programme.

The *cacao* CP-III cDNA sequence is 1768 bp long. A putative initiation start codon was assigned by comparison with other carboxypeptidase sequences. It is located 25 bp from the 5' end. The open reading frame is broken by a stop codon (TGA) at position 1549, followed by a putative polyadenylation signal (TATAAA) at position 1725.

Figure 3A:
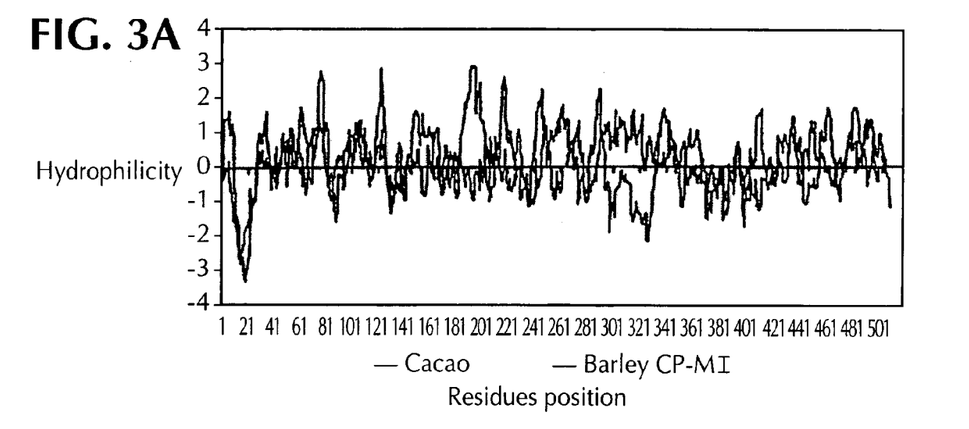
FIG. 3 shows a comparison of the hydrophilicity Plot-Kyte-Doolittle for the *cacao* CP-III sequence with Barley CP-MI, CP-MII and CP-MIII.
Figure 3B:
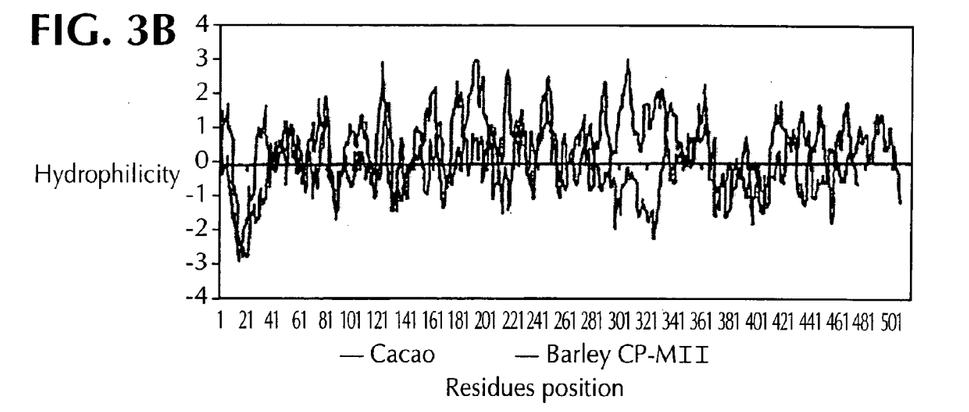
Figure 3C:
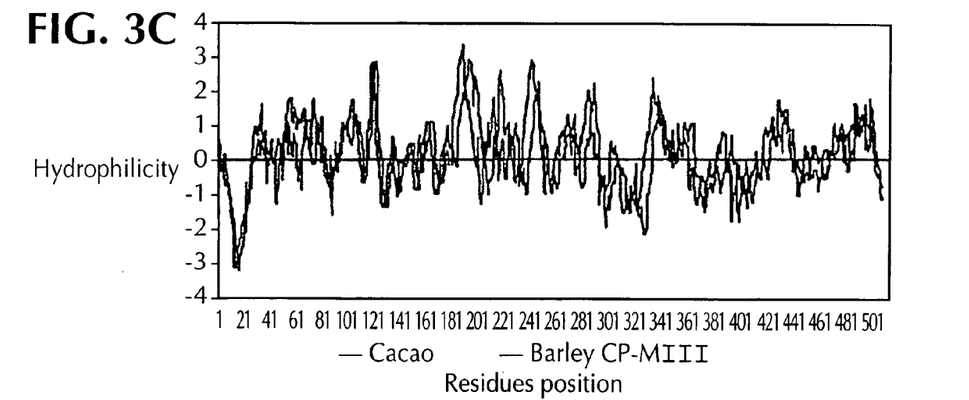

*Cacao* CP-III encodes a 508 amino acid type III carboxypeptidase C with a predicted molecular weight of 56 kDa and a pH of 5.04. The catalytic amino acids are present at position $Ser^{228}$, $Asp^{416}$ and $His^{473}$. A hydrophilicity analysis was performed using a Lasergene program (DNASTAR) and a window of 9. The results of a comparison of the hydrophiliccity Plot-Kyte-Doolittle for the *cacao* CP-III sequence with Barley CP-MI, CP-MII AND CP-MIII (FIG. 3) reveals that *cacao* CP-III encodes a hydrophilic protein with a very hydrophobic N-terminal end, indicating the presence of a signal peptide.

Northern Blot Analysis

Figure 4A:
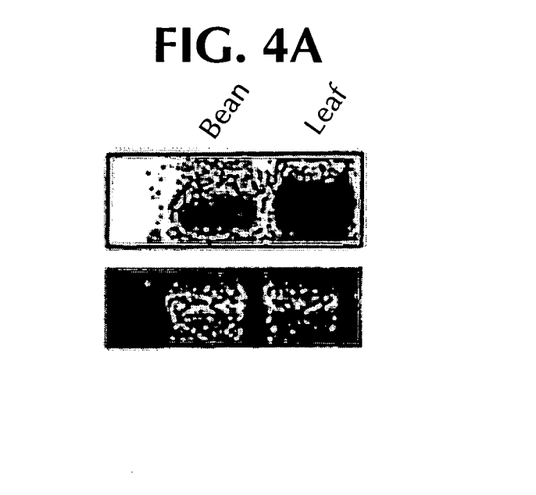
FIGS. 4A, 4B and 4C shows a Northern blot analysis of *cacao* CP-III.
Figure 4B:
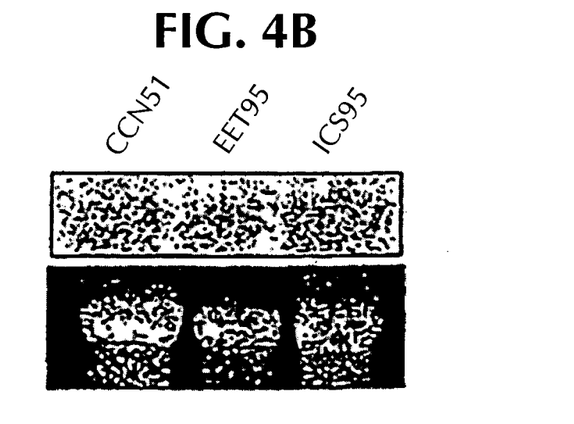
Figure 4C:
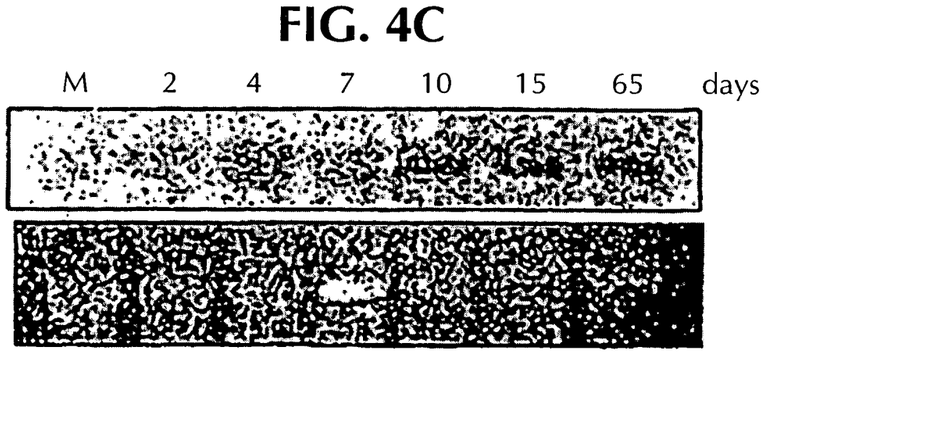

Total RNA samples were separated on 1.5% agarose gel containing 6% formaldehyde. RNA was separated on agarose gels, then transferred to a nylon membrane and probed with radiolabelled *cacao* CP-III cDNA under stringent hybridization conditions. An equal loading of the RNA samples was confirmed by ethidium bromide staining of ribosomal RNA in the gel before transfer to the membrane (FIG. 4). After electrophoresis, RNA was blotted onto nylon membranes (Appligene) and hybridized with $^{32}$P-labeled *cacao* CP-III probe at 65° C. in 250 mM Na-phosphate buffer pH 7.2, 6.6% SDS, 1 mM EDTA and 1% BSA. Cacao CP-III cDNA fragment was amplified by PCR using pCP8 and pCP7R primers and labelled by the random priming procedure (rediprime™ II, Amersham Pharmacia Biotech). Membranes were washed three times at 65° C. for 30 min in 2×SSC, 0.1% SDS, in 1×SSC, 0.1% SDS and in 0.5×SSC, 0.1% SDS. FIG. 4A illustrates the total RNA (15 µg per lane) from seed and leaf. FIG. 4B illustrates the total mature seed (15 µg per lane) from different *T. cacao* clones while FIG. 4C illustrates total RNA (15 µg per lane) from seed at different stages of germination.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A method for producing a cocoa flavor precursor, the method comprising:
    subjecting a cocoa component selected from the group consisting of *cacao* bean, *cacao* pulp, *cacao* storage protein and combinations thereof to an enzymatic degradation by a carboxypeptidase encoded by SEQ. ID. No 1 or functional variants thereof having a degree of homology of more than 90% to SEQ. ID. No. 1 wherein said variants code for a carboxypeptide to obtain the cocoa flavor precursor.

2. A method for manufacturing a cocoa liquor, the method comprising:
    subjecting a cocoa component selected from the group consisting of *cacao* bean, *cacao* pulp, *cacao* storage protein and combinations thereof to an enzymatic degradation by a carboxypeptidase encoded by SEQ. ID. No 1 or functional variants thereof having a degree of homology of more than 90% to SEQ. ID. No. 1 wherein said variants code for a carboxypeptide to obtain cocoa flavor precursors; and
    incorporating the cocoa component as part of a cocoa liquor.

3. A method for manufacturing a chocolate, the method comprising
    subjecting a cocoa component selected from the group consisting of *cacao* bean, *cacao* pulp, *cacao* storage protein and combinations thereof to an enzymatic degradation by a carboxypeptidase encoded by SEQ. ID. No 1 or functional variants thereof having a degree of homology of more than 90% to SEQ. ID. No. 1 wherein said variants code for a carboxypeptide to obtain cocoa flavor precursors; and
    incorporating the cocoa component as part of a chocolate.

4. A process for producing a cocoa flavor, the process comprising:
    subjecting a cocoa component selected from the group consisting of *cacao* bean, *cacao* pulp, *cacao* storage protein and combinations thereof to an enzymatic degradation by a carboxypeptidase encoded by SEQ. ID. No 1 or functional variants thereof having a degree of homology of more than 90% to SEQ. ID. No. 1 wherein said variants code for a carboxypeptide to obtain cocoa flavor precursors; and
    incorporating the cocoa component as part of a cocoa flavor.

* * * * *

SEQUENCE LISTING

```
<160> NUMBER OF SEQ ID NOS: 6

<210> SEQ ID NO 1
<211> LENGTH: 1768
<212> TYPE: DNA
<213> ORGANISM: Theobroma cacao

<400> SEQUENCE: 1
gactctcaaa gagaaaaaga aaagatggca aatccgaaaa tcttataccc gttttctgtt      60
tcccttctct tcctcatttc catctcctcc gcggccgctt cctccttctt agacgagcgg     120
cgactcggag gatcaagttt cccctcgata catgcgaaga agttgataag ggagttgaat     180
ttgtttccta aggaggaagt caacgtcgtt gatggaggcc aggtttcctt accggaggat     240
tcgaggttgg tggagaagcg gttcaagttc ccgaatttgg cggtgcctgg tggggtttcc     300
gttgaggatt tgggtcatca tgctggttat tacaagctag ctaattctca tgatgccaga     360
atgttctatt tcttctttga atcacgaaat agcaaaaagg accctgttgt aatctggttg     420
actggagggc cagggtgtag tagtgaattg gctttgtttt atgaaaatgg tcctttacc      480 attgctgaga acatgtctct tatttggaat cagtatggtt gggacatggc atcaaacctt     540
ctgtatgtgg accaacccat tggtaccggc tttagttata gttctgatag aagggacatt     600
cgtcataatg aagatgaagt tagcaacgac ctatatgact tcttacaggc attctttgct     660
gaacaccctg agtttgaaaa gaatgacttt tatataactg gagaatcata tgctgggcac     720
tacattccag cttttgctgc ccgagtccac caaggaaaca aagctaaaga tggaattcat     780
ataaacctaa agggatttgc tattggtaat ggcctgactg accctgcaat ccagtataaa     840
gcttacacag attatgcttt ggacatgggg gtaattaaga agtctgacta caatcgtatc     900
aacaagctgg ttccagtttg tgaaatggca ataaagctttt gtggcactga tggcacaatc     960
tcttgcatgg cttcatattt tgtctgcaat gccatattca ctggcatcat ggcacttgct    1020
ggcgatacaa attactacga cattagaacg aaatgtgaag ggagcctttg ctatgacttc    1080
tcaaacatgg agacatttct gaaccaggaa tctgttaggg atgcccttgg agttgggagt    1140
attgactttg tgtcctgcag tcctacagtg tatcaggcca tgctggttga ctggatgagg    1200
aatcttgaag ttggcattcc tgctctcctt gaggatggtg tcaagcttct tgtatatgct    1260
ggagaatatg atctcatctg caactggctt ggcaattcga gatgggtcca tgcaatggaa    1320
```

```
tggtctggtc agaaggagtt tgtagcatct cctgaggttc cttttgtcgt tgatggctca    1380
gaagcaggag tcttgagaac tcatggacct cttggtttcc taaaggttca cgatgcaggt    1440
cacatggttc ctatggacca gccaaaggca gcattggaga tgctgaagcg gtggactaag    1500
ggtacattat ctgaagctgc cgattcagag aaattggttg ctgaaatatg atttccatca    1560
ttgcactgct tgcatacaat ttagttggca ttagaatggg aatagccgta tcgtaaagct    1620
ctggggtttc tatgtatgcc tgtaaataat tgcatgttaa tgctagtaca atggtatctt    1680
tgttttttga agatcaccta ctgaacttat atgaatcaag gacttataaa aatcttctaa    1740
aaaaaaaaaa aaaaaaaaaa aaaaaaa                                        1768
```

<210> SEQ ID NO 2
<211> LENGTH: 508
<212> TYPE: PRT
<213> ORGANISM: Theobroma cacao

<400> SEQUENCE: 2

```
Met Ala Asn Pro Lys Ile Leu Tyr Pro Phe Ser Val Ser Leu Leu Phe
1               5                   10                  15

Leu Ile Ser Ile Ser Ser Ala Ala Ser Ser Phe Leu Asp Glu Arg
            20                  25                  30

Arg Leu Gly Gly Ser Ser Phe Pro Ser Ile His Ala Lys Lys Leu Ile
        35                  40                  45

Arg Glu Leu Asn Leu Phe Pro Lys Glu Val Asn Val Val Asp Gly
    50                  55                  60

Gly Gln Val Ser Leu Pro Glu Asp Ser Arg Leu Val Glu Lys Arg Phe
65                  70                  75                  80

Lys Phe Pro Asn Leu Ala Val Pro Gly Gly Val Ser Val Glu Asp Leu
                85                  90                  95

Gly His His Ala Gly Tyr Tyr Lys Leu Ala Asn Ser His Asp Ala Arg
            100                 105                 110

Met Phe Tyr Phe Phe Phe Glu Ser Arg Asn Ser Lys Lys Asp Pro Val
        115                 120                 125

Val Ile Trp Leu Thr Gly Gly Pro Gly Cys Ser Ser Glu Leu Ala Leu
130                 135                 140

Phe Tyr Glu Asn Gly Pro Phe Thr Ile Ala Glu Asn Met Ser Leu Ile
145                 150                 155                 160

Trp Asn Gln Tyr Gly Trp Asp Met Ala Ser Asn Leu Leu Tyr Val Asp
                165                 170                 175

Gln Pro Ile Gly Thr Gly Phe Ser Tyr Ser Ser Asp Arg Arg Asp Ile
            180                 185                 190

Arg His Asn Glu Asp Glu Val Ser Asn Asp Leu Tyr Asp Phe Leu Gln
        195                 200                 205

Ala Phe Phe Ala Glu His Pro Glu Phe Glu Lys Asn Asp Phe Tyr Ile
    210                 215                 220

Thr Gly Glu Ser Tyr Ala Gly His Tyr Ile Pro Ala Phe Ala Ala Arg
225                 230                 235                 240

Val His Gln Gly Asn Lys Ala Lys Asp Gly Ile His Ile Asn Leu Lys
                245                 250                 255

Gly Phe Ala Ile Gly Asn Gly Leu Thr Asp Pro Ala Ile Gln Tyr Lys
            260                 265                 270

Ala Tyr Thr Asp Tyr Ala Leu Asp Met Gly Val Ile Lys Lys Ser Asp
        275                 280                 285

Tyr Asn Arg Ile Asn Lys Leu Val Pro Val Cys Glu Met Ala Ile Lys
```

-continued

```
                    290                 295                 300
Leu Cys Gly Thr Asp Gly Thr Ile Ser Cys Met Ala Ser Tyr Phe Val
305                 310                 315                 320

Cys Asn Ala Ile Phe Thr Gly Ile Met Ala Leu Ala Gly Asp Thr Asn
                325                 330                 335

Tyr Tyr Asp Ile Arg Thr Lys Cys Glu Gly Ser Leu Cys Tyr Asp Phe
            340                 345                 350

Ser Asn Met Glu Thr Phe Leu Asn Gln Glu Ser Val Arg Asp Ala Leu
        355                 360                 365

Gly Val Gly Ser Ile Asp Phe Val Ser Cys Ser Pro Thr Val Tyr Gln
370                 375                 380

Ala Met Leu Val Asp Trp Met Arg Asn Leu Glu Val Gly Ile Pro Ala
385                 390                 395                 400

Leu Leu Glu Asp Gly Val Lys Leu Leu Val Tyr Ala Gly Glu Tyr Asp
                405                 410                 415

Leu Ile Cys Asn Trp Leu Gly Asn Ser Arg Trp Val His Ala Met Glu
            420                 425                 430

Trp Ser Gly Gln Lys Glu Phe Val Ala Ser Pro Glu Val Pro Phe Val
        435                 440                 445

Val Asp Gly Ser Glu Ala Gly Val Leu Arg Thr His Gly Pro Leu Gly
    450                 455                 460

Phe Leu Lys Val His Asp Ala Gly His Met Val Pro Met Asp Gln Pro
465                 470                 475                 480

Lys Ala Ala Leu Glu Met Leu Lys Arg Trp Thr Lys Gly Thr Leu Ser
                485                 490                 495

Gln Ala Ala Asp Ser Glu Lys Leu Val Ala Glu Ile
            500                 505

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: misc_feature
<222> LOCATION: (12)..(12)
<223> OTHER INFORMATION: any
<220> FEATURE:
<221> NAME/KEY: misc_feature
<222> LOCATION: (15)..(15)
<223> OTHER INFORMATION: any

<400> SEQUENCE: 3
ggytgrtcca tnggnaccat                                           20

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 4
gcttttgctg cccgagtcca cc                                        22

<210> SEQ ID NO 5
<211> LENGTH: 23
<212> TYPE: DNA
<213> ORGANISM: Artificial Sequence
<220> FEATURE:
```

-continued

```
<223> OTHER INFORMATION: Description of Artificial Sequence: Primer

<400> SEQUENCE: 5
caaagagaaa aagaaaagat ggc                                           23

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 6
ccccagagct ttacgatacg g                                             21
```